United States Patent [19]
Shapiro

[11] Patent Number: 6,150,152
[45] Date of Patent: Nov. 21, 2000

[54] HUMAN MACROPHAGE METALLOELASTASE

[75] Inventor: Steven D. Shapiro, St. Louis, Mo.

[73] Assignee: Washington University, St. Louis, Mo.

[21] Appl. No.: 08/068,392

[22] Filed: May 28, 1993

[51] Int. Cl.[7] .............................. C12N 9/66; C07H 21/04
[52] U.S. Cl. ..................... 435/218; 435/183; 435/212; 536/23.2
[58] Field of Search ................................. 536/23.1, 23.2, 536/23.5; 436/320.1, 91, 218; 930/240; 935/9, 10, 11, 14

[56] References Cited

U.S. PATENT DOCUMENTS 5,223,425  6/1993  Flier et al. ......................... 435/240.2

OTHER PUBLICATIONS

Shapiro et al. 1992. J. Biol. Chem. 267, 4664–4671.

*Primary Examiner*—Ponnathapu Achutamurthy
*Assistant Examiner*—Manjunath N. Rao
*Attorney, Agent, or Firm*—Scott J. Meyer

[57] ABSTRACT

A novel 54 kDa human macrophage metalloelastase (HME) having elastolytic activity and the cDNA which encodes for this enzyme are disclosed.

2 Claims, 11 Drawing Sheets

HMEMKFLL-ILLLQATASGALPLNSSTSLEKNNVLFGERYLEKFYGLEINKLPVTKMKYSG
MMEMKFLMMIVFLQVSACGAAPMNDS---E------FAEWYLSRFYDYGKDRIPMTKTKTNR

NLMKEKIQEMQHFLGLKVTGQLDTSTLEMMHAPRCGVPDVHHFREMPGGPVWRKHYITYR
NFLKEKLQEMQQFFGLEATGQLDNSTLAIMHIPRCGVPDVQHLRAVPQRSRWMKRYLTYR

INNYTPDMNREDVDYAIRKAFQVWSNVTPLKFSKINTGMADILVVFARGAHGDFHAFDGK
IYNYTPDMKREDVDYIFQKAFQVWSDVTPLRFRKLHKDEADIMILFAFGAHGDFNYFDGK

GGILAHAFGPGSGIGGDAHFDEDEFWTTHSGGTNLFLTAVHEIGHSLGLGHSSDPKAVMF
GGTLAHVFYPGPGIQGDAHFDEAETWTKSFQGTNLFLVAVHELGHSLGLQHSNNPKSIMY

PTYKYVDINTFRLSADDIRGIQSLYGDPKENQRLPNPDNSEP-ALCDPNLSFDAVTTVGN
PTYRYLNPSTFRLSADDIRNIQSLYGAPVKPPSLTKPS-SPPSTFCHQSLSFDAVTTVGE

KIFFFKDRFFWLKVSERPKTSVNLISSLWPTLPSGIEAAYEIEARNQVFLFKDDKYWLIS
KILFFFKDWFFWWKLPGSPATNITSISSIWPSIPSAIQAAYEIESRNQLFLFKDEKYWLIN

NLRPEPNYPKSIHSFGFPNEVKKIDAAVENPRFYRTYFFVDNQYWRYDERRQMMDPGYPK
NLVPEPHYPRSIYSLGFSASVKKVDAAVFDPLRQKVYFFVDXHYWRYDVRQELMDPAYPK

LITKNFQGIGPKIDAVFYSKNKYYFFQGSNQFEYDFLLQRITKTLKSNSWFGC
LFSTHFPGIKPMIDAVLYFKRHYYIF-QGAYQLEIDPLFRRVTKTLKSTSWFGC

```
            10         20         30         40         50         60
ATGAAGTTTCTTCTAATACTGCTCCTGCAGGCCACTGCTTCTGGAGCTCTTCCCCTGAAC
MetLysPheLeuLeuIleLeuLeuLeuGlnAlaThrAlaSerGlyAlaLeuProLeuAsn 70         80         90        100        110        120
AGCTCTACAAGCCTGGAAAAAAATAATGTGCTATTTGGTGAGAGATACTTAGAAAAATTT
SerSerThrSerLeuGluLysAsnAsnValLeuPheGlyGluArgTyrLeuGluLysPhe 130        140        150        160        170        180
TATGGCCTTGAGATAAACAAACTTCCAGTGACAAAAATGAAATATAGTGGAAACTTAATG
TyrGlyLeuGluIleAsnLysLeuProValThrLysMetLysTyrSerGlyAsnLeuMet 190        200        210        220        230        240
AAGGAAAAAATCCAAGAAATGCAGCACTTCTTGGGTCTGAAAGTGACCGGGCAACTGGAC
LysGluLysIleGlnGluMetGlnHisPheLeuGlyLeuLysValThrGlyGlnLeuAsp 250        260        270        280        290        300
ACATCTACCCTGGAGATGATGCACGCACCTCGATGTGGAGTCCCCGATGTCCATCATTTC
ThrSerThrLeuGluMetMetHisAlaProArgCysGlyValProAspValHisHisPhe 310        320        330        340        350        360
AGGGAAATGCCAGGGGGGCCCGTATGGAGGAAACATTATATCACCTACAGAATCAATAAT
ArgGluMetProGlyGlyProValTrpArgLysHisTyrIleThrTyrArgIleAsnAsn 370        380        390        400        410        420
TACACACCTGACATGAACCGTGAGGATGTTGACTACGCAATCCGGAAAGCTTTCCAAGTA
TyrThrProAspMetAsnArgGluAspValAspTyrAlaIleArgLysAlaPheGlnVal 430        440        450        460        470        480
TGGAGTAATGTTACCCCCTTGAAATTCAGCAAGATTAACACAGGCATGGCTGACATTTTG
TrpSerAsnValThrProLeuLysPheSerLysIleAsnThrGlyMetAlaAspIleLeu 490        500        510        520        530        540
GTGGTTTTTGCCCGTGGAGCTCATGGAGACTTCCATGCTTTTGATGGCAAAGGTGGAATC
ValValPheAlaArgGlyAlaHisGlyAspPheHisAlaPheAspGlyLysGlyGlyIle
```

FIG. 5A

```
          550       560       570       580       590       600
       CTAGCCCATGCTTTTGGACCTGGATCTGGCATTGGAGGGGATGCACATTTCGATGAGGAC
       LeuAlaHisAlaPheGlyProGlySerGlyIleGlyGlyAspAlaHisPheAspGluAsp 610       620       630       640       650       660
       GAATTCTGGACTACACATTCAGGAGGCACAAACTTGTTCCTCACTGCTGTTCACGAGATT
       GluPheTrpThrThrHisSerGlyGlyThrAsnLeuPheLeuThrAlaValHisGluIle 670       680       690       700       710       720
       GGCCATTCCTTAGGTCTTGGCCATTCTAGTGATCCAAAGGCTGTAATGTTCCCCACCTAC
       GlyHisSerLeuGlyLeuGlyHisSerSerAspProLysAlaValMetPheProThrTyr 730       740       750       760       770       780
       AAATATGTCGACATCAACACATTTCGCCTCTCTGCTGATGACATACGTGGCATTCAGTCC
       LysTyrValAspIleAsnThrPheArgLeuSerAlaAspAspIleArgGlyIleGlnSer 790       800       810       820       830       840
       CTGTATGGAGACCCAAAAGAGAACCAACGCTTGCCAAATCCTGACAATTCAGAACCAGCT
       LeuTyrGlyAspProLysGluAsnGlnArgLeuProAsnProAspAsnSerGluProAla 850       860       870       880       890       900
       CTCTGTGACCCCAATTTGAGTTTTGATGCTGTCACTACCGTGGGAAATAAGATCTTTTTC
       LeuCysAspProAsnLeuSerPheAspAlaValThrThrValGlyAsnLysIlePhePhe 910       920       930       940       950       960
       TTCAAAGACAGGTTCTTCTGGCTGAAGGTTTCTGAGAGACCAAAGACCAGTGTTAATTTA
       PheLysAspArgPhePheTrpLeuLysValSerGluArgProLysThrSerValAsnLeu 970       980       990      1000      1010      1020
       ATTTCTTCCTTATGGCCAACCTTGCCATCTGGCATTGAAGCTGCTTATGAAATTGAAGCC
       IleSerSerLeuTrpProThrLeuProSerGlyIleGluAlaAlaTyrGluIleGluAla 1030      1040      1050      1060      1070      1080
       AGAAATCAAGTTTTTCTTTTTAAAGATGACAAATACTGGTTAATTAGCAATTTAAGACCA
       ArgAsnGlnValPheLeuPheLysAspAspLysTyrTrpLeuIleSerAsnLeuArgPro
```

FIG. 5B

```
     1090      1100      1110      1120      1130      1140
GAGCCAAATTATCCCAAGAGCATACATTCTTTTGGTTTTCCTAACTTTGTGAAAAAAATT
GluProAsnTyrProLysSerIleHisSerPheGlyPheProAsnPheValLysLysIle 1150      1160      1170      1180      1190      1200
GATGCAGCTGTTTTTAACCCACGTTTTTATAGGACCTACTTCTTTGTAGATAACCAGTAT
AspAlaAlaValPheAsnProArgPheTyrArgThrTyrPhePheValAspAsnGlnTyr 1210      1220      1230      1240      1250      1260
TGGAGGTATGATGAAAGGAGACAGATGATGGACCCTGGTTATCCCAAACTGATTACCAAG
TrpArgTyrAspGluArgArgGlnMetMetAspProGlyTyrProLysLeuIleThrLys 1270      1280      1290      1300      1310      1320
AACTTCCAAGGAATCGGGCCTAAAATTGATGCAGTCTTCTACTCTAAAAACAAATACTAC
AsnPheGlnGlyIleGlyProLysIleAspAlaValPheTyrSerLysAsnLysTyrTyr 1330      1340      1350      1360      1370      1380
TATTTCTTCCAAGGATCTAACCAATTTGAATATGACTTCCTACTCCAACGTATCACCAAA
TyrPhePheGlnGlySerAsnGlnPheGluTyrAspPheLeuLeuGlnArgIleThrLys 1390      1400      1410      1420      1430      1440
ACACTGAAAAGCAATAGCTGGTTTGGTTGTTAGAAATGGTGTAATTAATGGTTTTTGTTA
ThrLeuLysSerAsnSerTrpPheGlyCysEnd 1450      1460      1470      1480      1490      1500
GTTCACTTCAGCTTAATAAGTATTTATTGCATATTTGCTATGTCCTCAGTGTACCACTAC 1510      1520      1530      1540      1550      1560
TTAGAGATATGTATCATAAAAATAAAATCTGTAAACCATAGGTAATGATTATATAAAATA 1570      1580      1590      1600      1610      1620
CATAATATTTTTCAATTTTGAAAACTCTAATTGTCCATTCTTGCTTGACTCTACTATTAA
```

FIG. 5C

```
         1630      1640      1650      1660      1670      1680
GTTTGAAAATAGTTACCTTCAAAGCAAGAGAATTCTATTTGAAGCATGCTCTGTAAGTTG 1690      1700      1710      1720      1730      1740
CTTCCTAACATCCTTGGACTGAGAAATTATACTTACTTCTGGCATAACTAAAATTAAGTA 1750      1760      1770      1780      1790      1800
TATATATTTTGGCTCAAATAAAATTGAAAAAAAAAAAAACTTTAGAGCACACTGGCGGCC

1810
GTTACTAGTGGATGCCGG
```

FIG. 5D

HUMAN MACROPHAGE METALLOELASTASE

This invention was made with Government support under grant number HL 29594 and CA 49712 awarded by the National Institutes of Health. The Government has certain rights in the invention.

BACKGROUND OF THE INVENTION

This invention relates to a novel human macrophage metalloproteinase having elastolytic activity and, more particularly, to the CDNA clone representing the 54 kDa proenzyme referred to herein as human macrophage metalloelastase (HME).

Metalloproteinases comprise a family of structurally related matrix degrading enzymes involved in normal embryonic development, growth, tissue remodeling, and tissue repair.

Macrophages participate in extracellular matrix turnover both directly by secretion of proteinases and proteinase inhibitors and indirectly by the elaboration of cytokines such as interleukin-1 or tumor necrosis factor, which induces proteinase production by resident fibroblasts. Human macrophages have the capacity to produce several metalloproteinases including interstitial collagenase, stromelysin, and two type IV collagenase/gelatinases of 92 and 72 kDa, of which 92 kDa enzyme represents the predominant macrophage product. The DNA cloning of interstitial collagenase and the two type IV-collagenase/gelatinases of 72 kDa and 92 kDa is described, e.g., in U.S. Pat. Nos. 4,772,557, 4,923,818 and 4,992,537, respectively. The DNA cloning of stromelysin is described in PCT Int. Appln. WO 87 07,907, published Dec. 30, 1987.

Macrophages also produce the counter-regulatory tissue inhibitors of metalloproteinases (TIMP-1 and TIMP-2), which are proteins that inhibit metalloproteinases via a high affinity, noncovalent bond. TIMP-2 and its homology to TIMP-1 are described in EP 404,750, published December 27, 1990 and in co-pending U.S. Application Ser. No. 07/358,043, filed May 26, 1989.

Elastin degradation and abnormal repair are pivotal events in the pathogenesis of pulmonary emphysema. Cigarette smoking, the predominant risk factor for emphysema, is associated with a large accumulation of macrophages in the lungs. Cigarette smoking is associated with a 10-fold increase in cells recovered by bronchoalveolar lavage [Hunninghake and Crystal, *Am. Rev. Resp. Dis.* 128, 833–838 (1990)] with macrophages comprising over 98% of cells and PMNs less than 1% [Merchant et al., *Ibid.* 146, 448–453 (1992)]. Moreover, macrophages are predominant in the respiratory bronchioles of cigarette smokers where emphysematous changes are first manifest [Niewoehner et al., *N. Engl. J. Med.* 291, 755–758 (1974)].

Recently, two classes of macrophage-derived proteinases have been implicated in elastolysis: (1) *Matrix metalloproteinases* (MMPs) that can degrade elastin include the 92 kDa gelatinase, an abundant macrophage product, and the 72 kDa gelatinase, secreted by many cell types but present in only trace amounts in macrophages [Welgus et al.,*J. Clin. Invest.* 86, 1496–1502 (1990); Murphy and Docherty,*Am. J. Respir. Cell Mol. Biol.* 7, 120–125 (1992); and Senior et al.,*J. Biol. Chem.* 266, 7870–7875 (1991)]. Matrilysin, another recently described metalloproteinase with elastolytic activity, is found in peripheral blood monocytes but not in alveolar macrophages [Busiek et al.,*J. Biol. Chem.* 267, 9087–9092 (1992)]. (2) *Cysteine proteinases* produced by macrophages that cleave elastin include cathepsin L [Reilly et al., *Biochem. J.* 257, 493–498 (1989)] and cathepsin S [Shi et al., *J. Biol. Chem.* 267, 7258–7262 (1992)], both of which are most active in acidic environments (~pH 5).

It has been reported that media conditioned by mouse peritoneal macrophages exhibited significant elastolytic activity [Werb and Gordon, *J. Exp. Med.* 142, 361–377 (1975)]. A 22 kDa, metal-dependent, elastolytic proteinase, termed mouse macrophage elastase (MME), was isolated [Banda and Werb, *Biochem. J.* 193, 589–605 (1981)]. However, despite the efforts of many investigators, human macrophage elastase activity could not be documented and many doubted its existence. The present inventor and colleagues recently cloned the MME cDNA and demonstrated that MME is truly a member of the MMP family [Shapiro et al.,*J. Biol. Chem.* 267, 4664–4671 (1992)]. Surprisingly, the molecular mass of the MME proenzyme is 53 kDa, similar to several other MMPs including the collagenases and stromelysins. The 22 kDa active form of MME, previously described, results from both classic N-terminal activation and unusual C-terminal processing. MME is less than 50% identical at the amino acid level to all known human MMPs.

BRIEF DESCRIPTION OF THE INVENTION

In accordance with the present invention the cDNA of a novel human macrophage metalloproteinase that possesses elastolytic activity has been cloned. The primary structure of the protein, termed human macrophage metalloelastase (HME), has been determined and characterized. The molecular mass of the HME proenzyme is 54 kDa with a 45 kDa N-terminal active form similar to mouse macrophage metalloelastase (MME). The CDNA sequence of ~1410 base pairs (bp) [SEQ ID NO:1] codes for the 470 amino acids of the full HME protein [SEQ ID NO:2] which has about 63% homology with the MME protein [SEQ ID NO:3]. The most closely related human metalloproteinases are stromelysin-1 and interstitial collagenase, each of which has about 49% homology to HME. The isolated HME thus is useful in a similar manner as these and other such known matrix metalloproteinases that have elastolytic activity. Elastolytic activity is demonstrated herein by conventional methodology for measuring elastin degradation by incubation with HME at 37° C.

DETAILED DESCRIPTION OF THE INVENTION

While the specification concludes with claims particularly pointing out and distinctly claiming the subject matter regarded as forming the invention, it is believed that the invention will be better understood from the following detailed description of preferred embodiments taken in conjunction with the appended drawings in which:

In FIG. 1A the HME sequence is compared with the mouse macrophage metalloelastase (MME) sequence.

FIG. 3, in two parts FIGS. 3A and 3B, shows the bacterial expression and elastolytic activity of recombinant HME.

FIG. 4, in two parts FIGS. 4A and 4B, shows HME secretion, processing and elastolytic activity from human alveolar macrophages. In FIG. 4A, human alveolar macrophages were obtained by bronchoalveolar lavage from a healthy cigarette smoker.

FIG. 5, in four parts FIGS. 5A, 5B, 5C and 5D, shows the cDNA sequence that codes for the HME protein of FIG. 1.

In order to illustrate specific preferred embodiments of the invention in greater detail, the following exemplary laboratory preparative work was carried out. However, it will be understood that the invention is not limited to these specific examples or the details described therein.

Standard biochemical nomenclature is used herein in which the nucleotide bases are designated as adenine (A); thymine (T); guanine (G); and cytosine (C). Corresponding nucleotides are, for example, deoxyadenosine-5'-triphosphate (dATP). As is conventional for convenience in the structural representation of a DNA nucleotide sequence, only one strand is usually shown in which A on one strand connotes T on its complement and G connotes C. Amino acids are shown either by three letter or one letter abbreviations as follows:

| Abbreviated | Designation | Amino Acid |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

EXAMPLES

A distinct orthologue to mouse metalloelastase (MME) with the capacity to degrade elastin, and which represents a novel human matrix metalloproteinase, was produced and tested as follows:

Human macrophage metalloelastase (HME) cDNA was cloned from a human alveolar macrophage plasmid library (provided by Harold Chapman, Peter Bent Brigham Hospital, Boston, MA) probed with a ~400 bp genomic fragment of HME containing exons 3 and 4 that was obtained as shown in the detailed description of FIG. 1, hereinbelow. HME cDNA is 72% identical to MME cDNA and contains an open reading frame of 1410 bp, followed by 350 bp of 3' untranslated sequence terminating with a polyadenylation signal and a poly A-tail (FIGS. 5A to 5D). The deduced amino acid sequence (FIG. 1A) demonstrates that HME is a distinct protein that can be organized into the typical MMP domain structure containing the highly conserved cysteine switch and zinc-binding motifs (FIG. 1B). The predicted molecular mass of the HME proenzyme is 54 kDa with a 45 kDa N-terminal active form, similar to MME. HME and MME are 63% identical at the amino acid level. The most closely related human MMPs are stromelysin-1 and interstitial collagenase; each is 49% identical to HME.

Northern hybridization was performed with total cellular RNA derived from human alveolar macrophages. Macrophages obtained from healthy cigarette smokers by bronchoalveolar lavage were maintained in culture for 24 hrs by conventional procedures as previously described by Shapiro et al., *J. Clin. Invest.* 86, 1204–1210 (1990). Using HME cDNA as the probe, a 1.8 kb mRNA species was detected (FIG. 2), confirming that the cDNA is nearly full-length and that the gene is transcribed. Furthermore, exposure of alveolar macrophages to lipopolysaccharide (LPS) increased steady-state mRNA levels, while treatment with dexamethasone reduced levels of HME mRNA. This pattern of regulation is identical to that of MME as described by Shapiro et al., *J. Biol. Chem.* 267, 4664–4671 (1992). HME mRNA was not detected in fresh peripheral blood monocytes.

Recombinant HME (rHME) was expressed in *E. coli* to determine whether HME cDNA encoded a proteinase with elastolytic activity. Production of rHME (both proenzyme and N-terminal active forms) in crude lysates is demonstrated in FIG. 3A by SDS/PAGE subjected to silver stain and Western hybridization using a peptide-derived antibody specific for HME. Lysates were incubated with insoluble $^3$H-elastin to quantify elastolytic activity by conventional procedures as described by Senior et al., *Am. Rev. Respir. Dis.* 139, 1251–1256 (1989) and Senior et al., *J. Biol. Chem.* 266, 7870–7875 (1991). Crude and partially purified lysates containing rHME were elastolytic, whereas the control lysates were not (FIG. 3B). Elastin degradation was inhibited by molar excess TIMP-1 but not by serine or cysteine proteinase inhibitors.

Figure 4A:
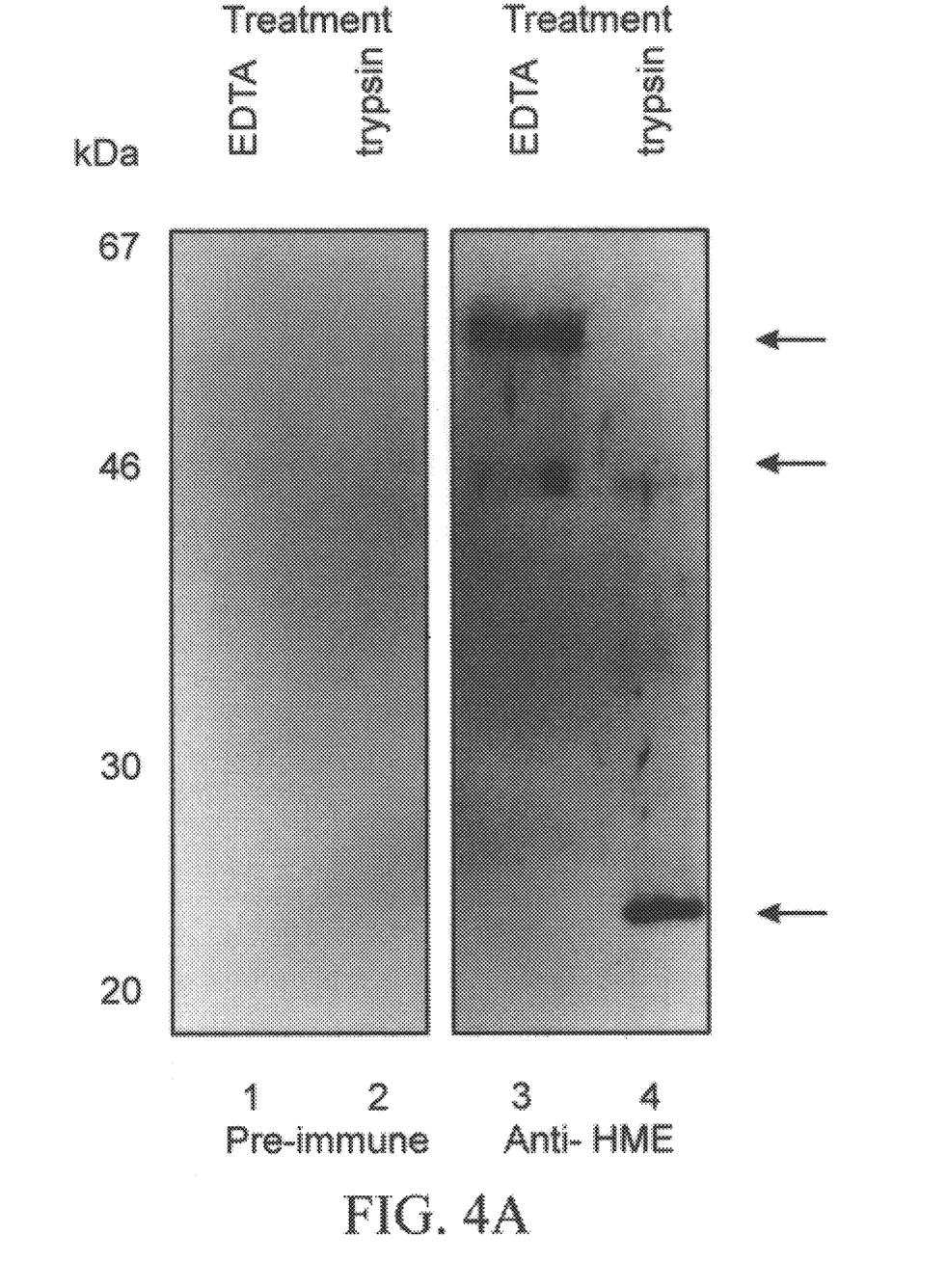
Figure 4B:
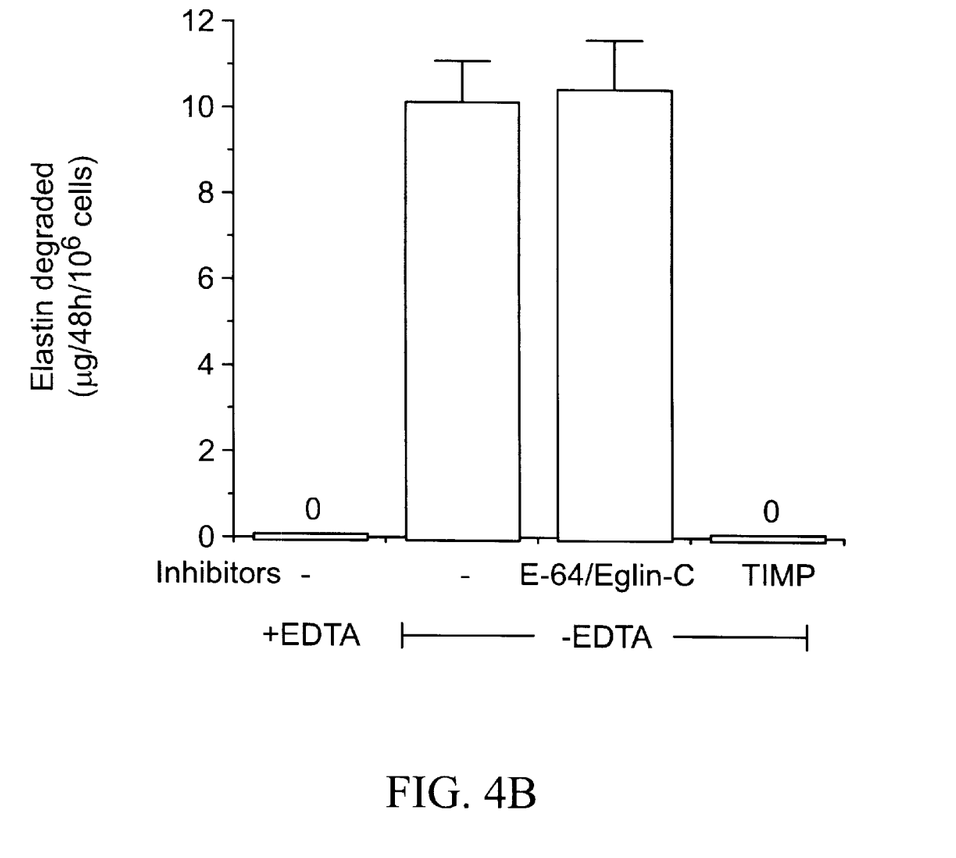
FIG. 4B is a graphical representation in which aliquots of HME-containing conditioned media following removal of gelatinase and inhibitors were incubated with insoluble $^3$H-elastin for 48 hrs. at 37° C. and solubilized products were counted in a scintillation counter to estimate degradation of elastin ($\mu$g/48 hrs/$10^6$ cells).
Figure 5A:
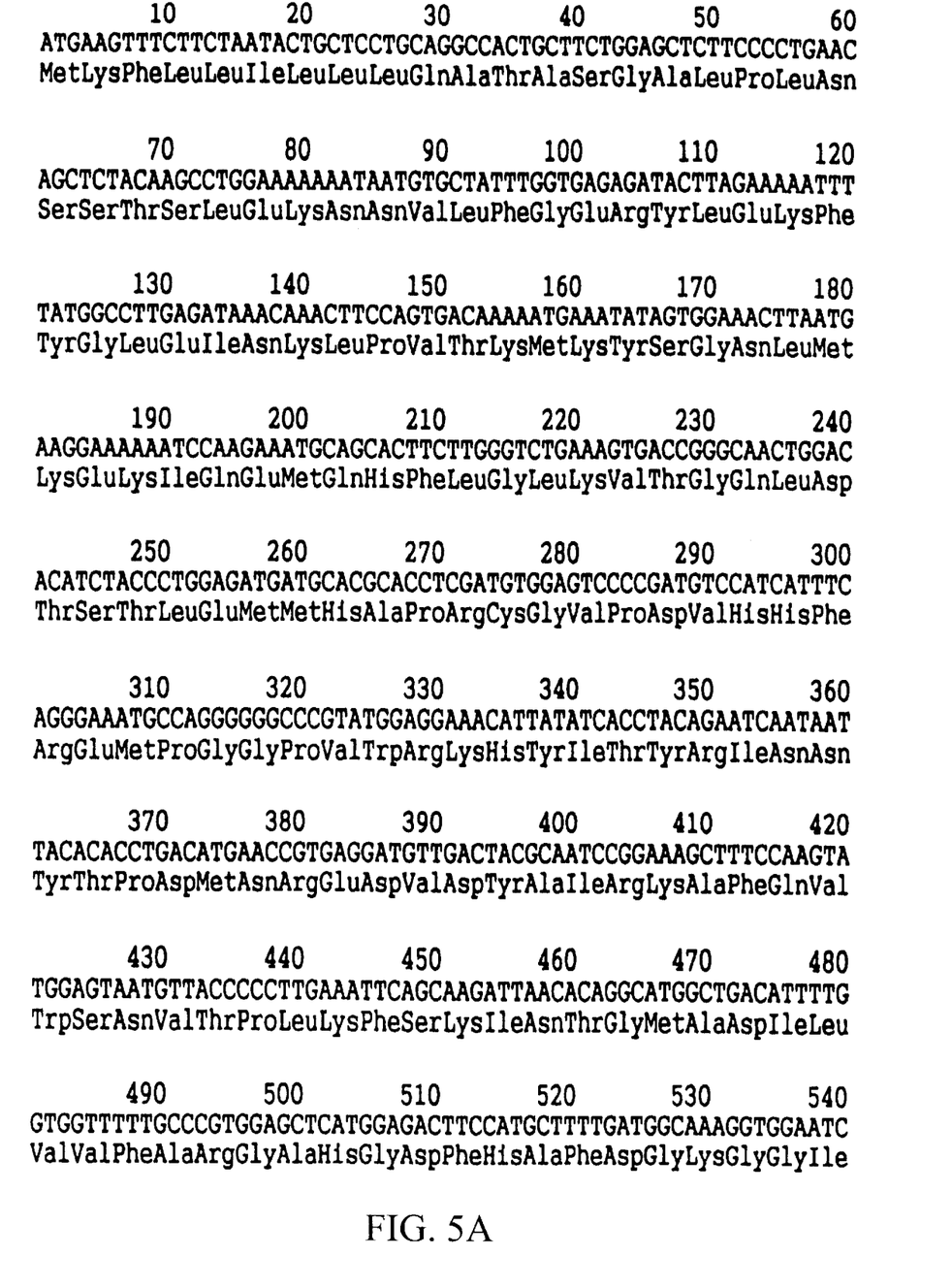
Figure 5B:
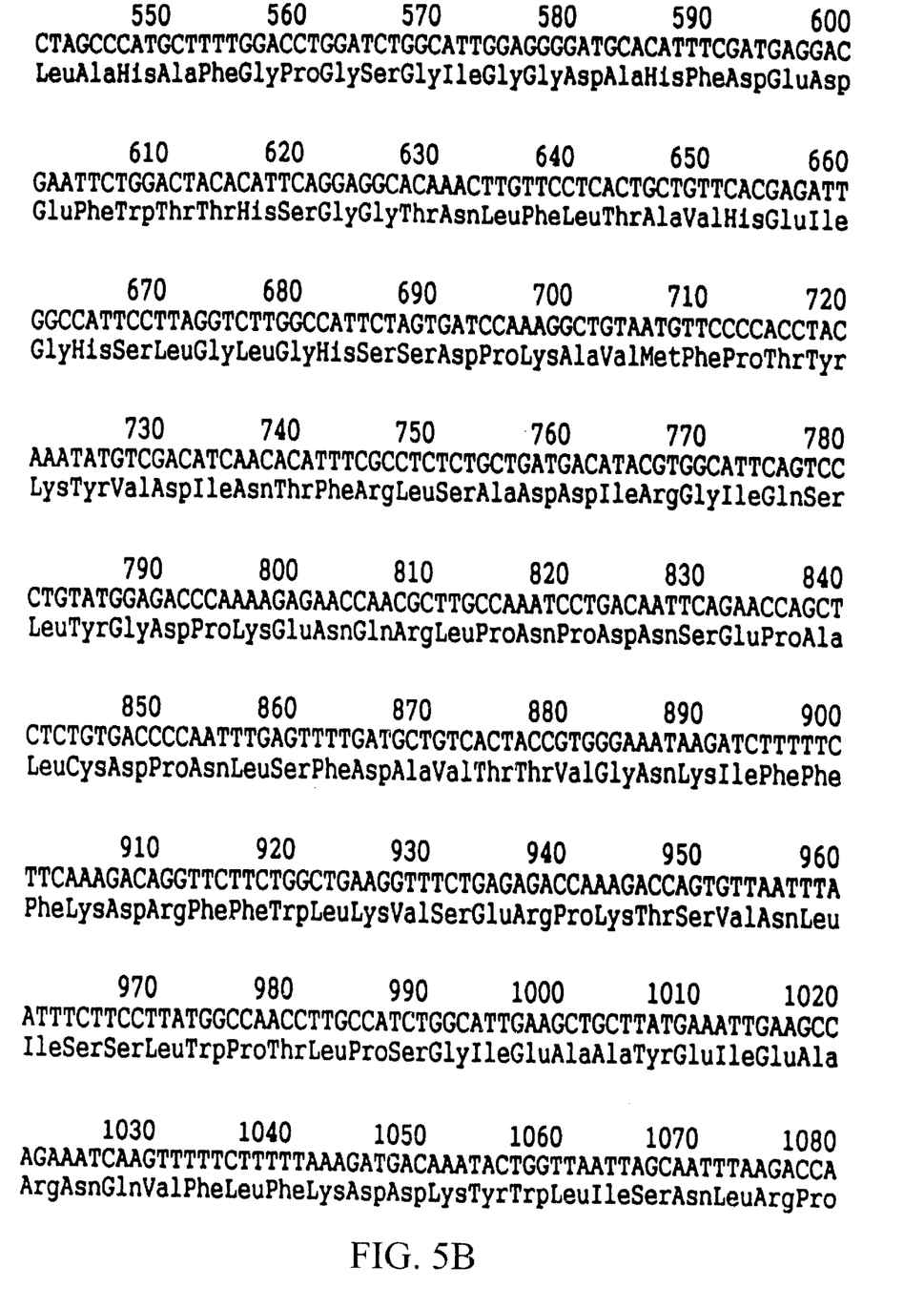
Figure 5C:
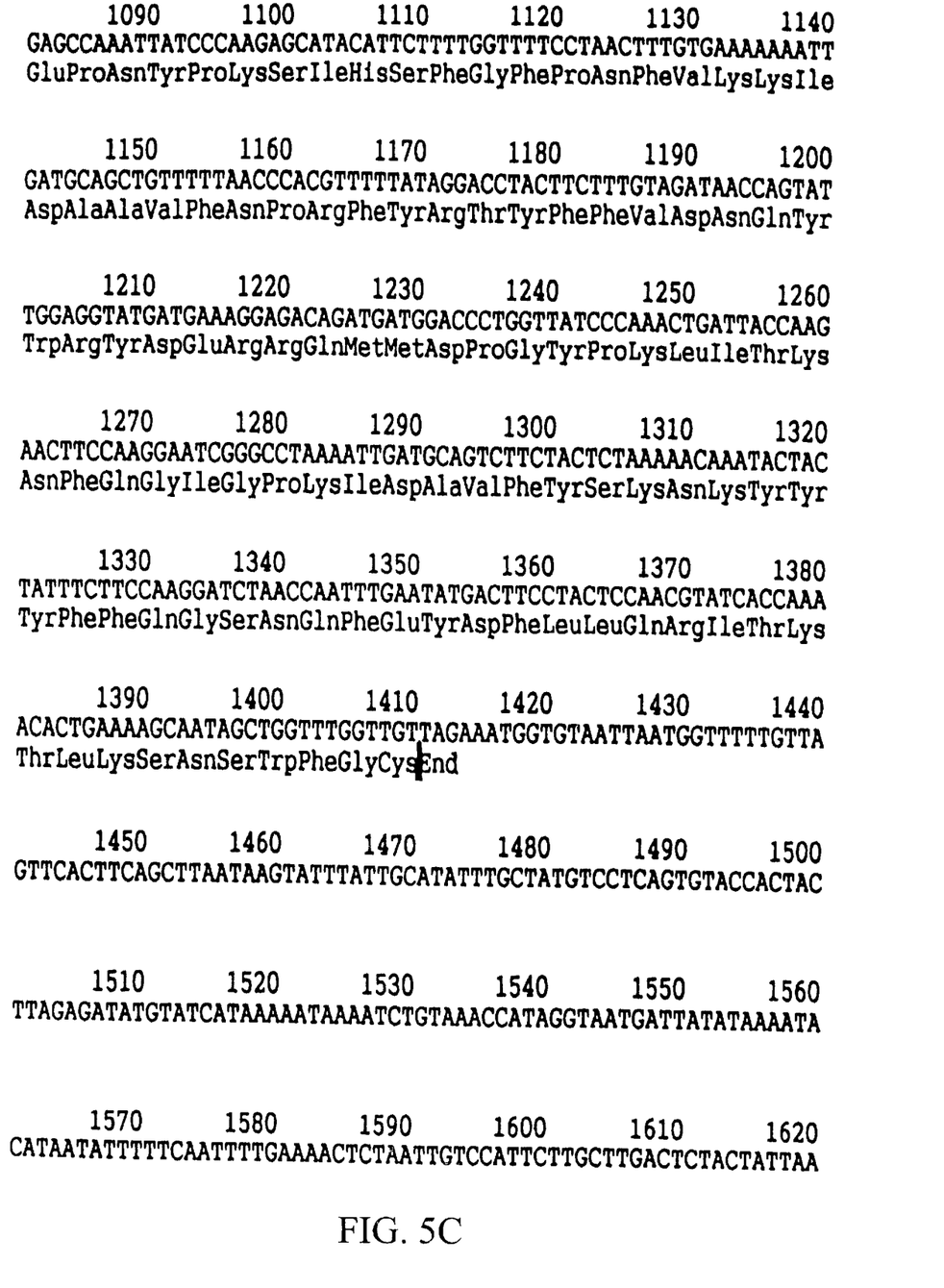
Figure 5D:
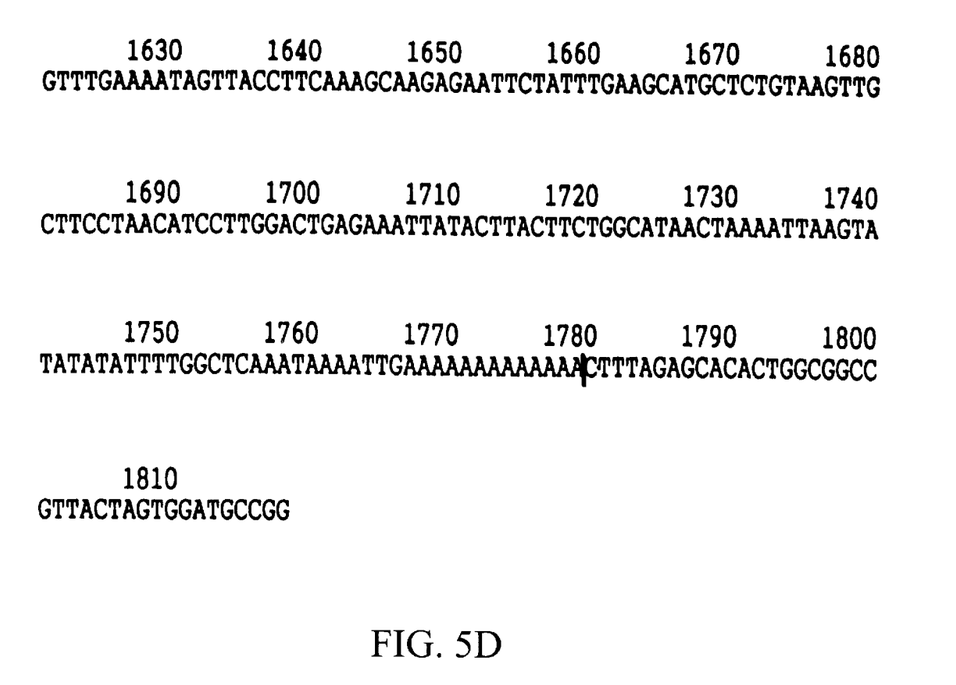

It is demonstrated herein that human alveolar macrophages express and secrete HME, and that native HME degrades elastin. Alveolar macrophages obtained by bronchoalveolar lavage were incubated in serum containing medium for 48 hrs. To remove both inhibitors and other released metalloelastases, conditioned media was passed over gelatin- and heparin-agarose columns. The elastolytic metalloproteinases, the 92 kDa and 72 kDa gelatinases, have a gelatin binding domain while HME does not. Consequently, it was found that a gelatin-agarose column bound all detectable gelatinase, but HME bound only to heparin-agarose. Partially purified proHME (maintained in proenzyme form with EDTA) migrated with a molecular mass of ~54 kDa as demonstrated by Western blot (FIG. 4A). Trypsin activation converted proHME to a truncated, mature 22 kDa form, analogous to the rapid N- and C-terminal processing exhibited by MME. Partially purified native HME degraded insoluble elastin (FIG. 4B). Elastolysis was inhibited by TIMP-1 and EDTA but not by serine or cysteine proteinase inhibitors. It is estimated that HME and the 92 kDa gelatinase each account for approximately one-half of macrophage-derived metalloelastase activity derived from the conditioned media of the alveolar macrophage cultures.

The procedures for producing and testing the disclosed MME are conveniently shown in the following detailed description of the accompanying figures.

Figure 1A:
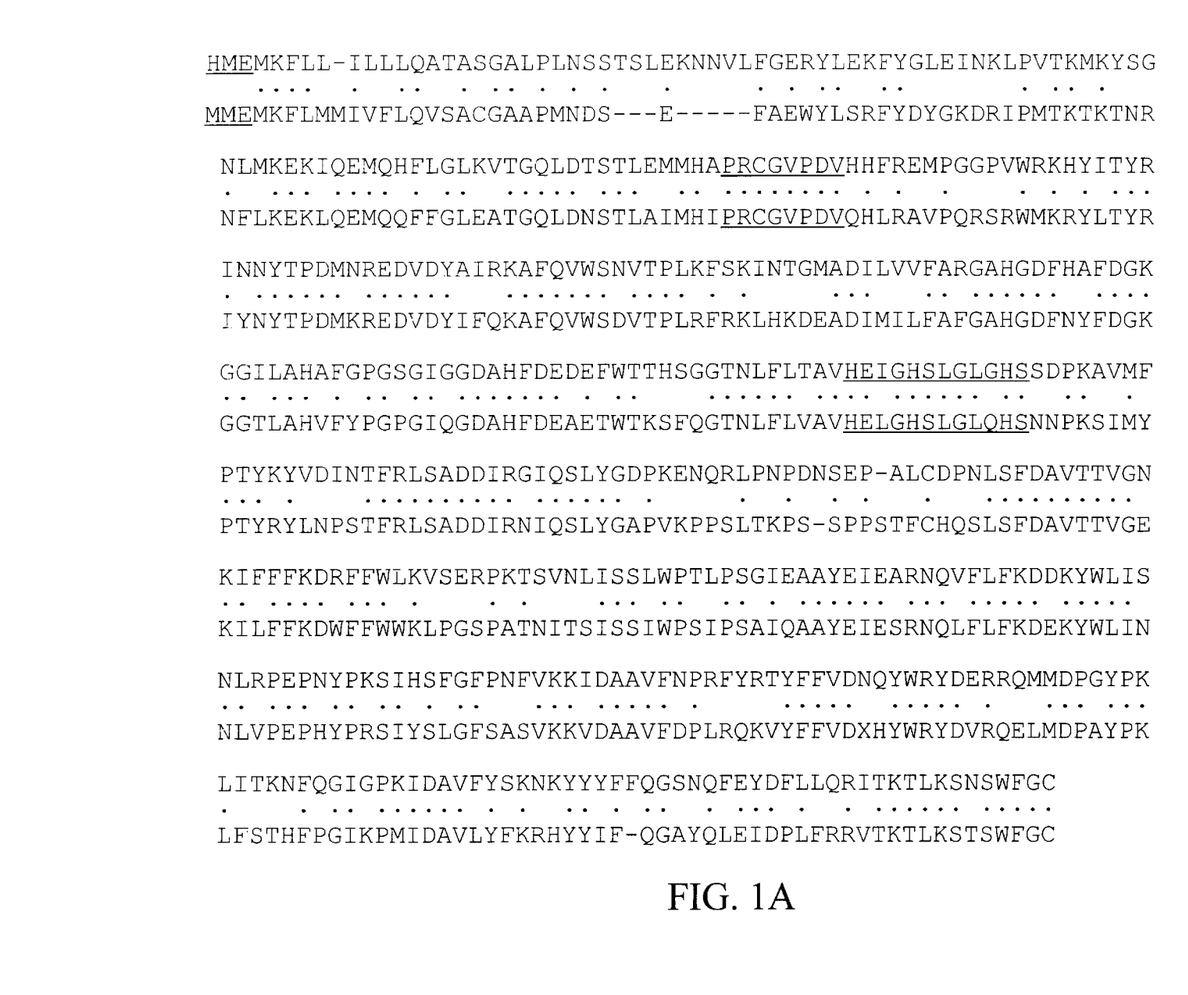
FIG. 1A shows the amino acid sequence and FIG. 1B shows the domain structure of the 54 kDa human macrophage metalloelastase (HME).
Figure 1B:
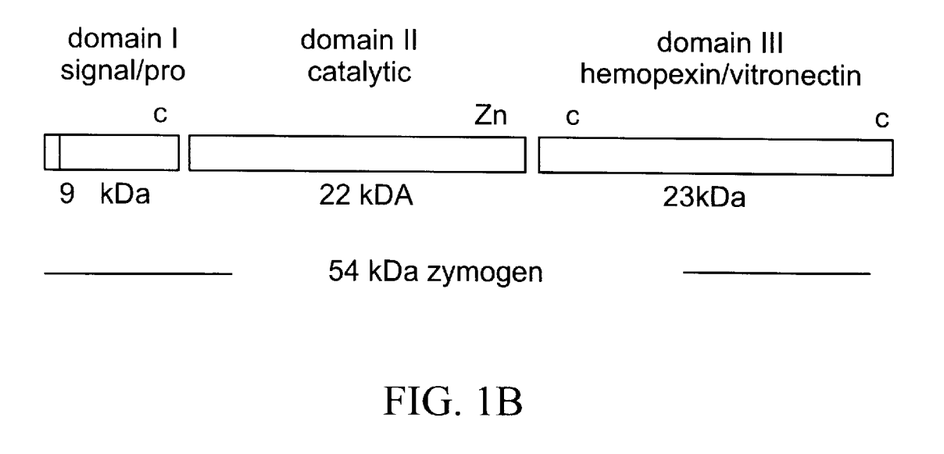

FIG. 1. Amino acid sequence and domain structure of HME. A. HME deduced amino acid sequence is compared with MME. These proteins are nearly identical in size and are 63% identical at the amino acid level, sharing highly related cysteine-switch and zinc-binding motifs (underlined). B. HME possesses a similar domain structure to MME, the stromelysins, and the interstitial collagenases. There is an N-terminal proenzyme domain (domain 1), a catalytic domain that coordinates the active site zinc molecule (domain II), and a C-terminal domain with weak homology to vitronectin and hemopexin (domain III). Methods: Prior to cloning human macrophage elastase (HME) cDNA, MME cDNA was used to screen a human genomic library (Clontech, Palo Alto, Calif.). A 6 kB EcoR1 fragment containing exons 1–4 was subcloned and sequenced. A genomic fragment containing exons 3 and 4 was radiolabeled and used as the probe to screen a human alveolar macrophage plasmid library constructed in the pcDNA 1 phagemid (provided by Harold Chapman, Peter Bent, Brigham Hospital, Boston, Mass.). 300,000 colonies were screened and 4 duplicate positives were purified. The largest contained near full-length cDNA that was subcloned into pUC9. The missing 5' end (~300 bp) was generated by reverse transcription and the polymerase chain reaction (using U937 RNA as the template) using reverse primers from the HME cDNA sequence and a forward primer just upstream from the translation initiation site based on genomic sequence. The amplified fragment was identical to the predicted genomic exonic sequence. This fragment was ligated in frame to the partial HME cDNA (using an overlapping HindIII site at bp 380). The entire cDNA (and appropriate genomic sequence) were sequenced on both strands using the dideoxy chain termination method of Sanger (with Sequenase 2.0, United States Biochemical, Corp., Cleveland, Ohio). The nucleotide sequence of MME is shown above the amino acid sequence in FIGS. 5A to 5D.

Figure 2:
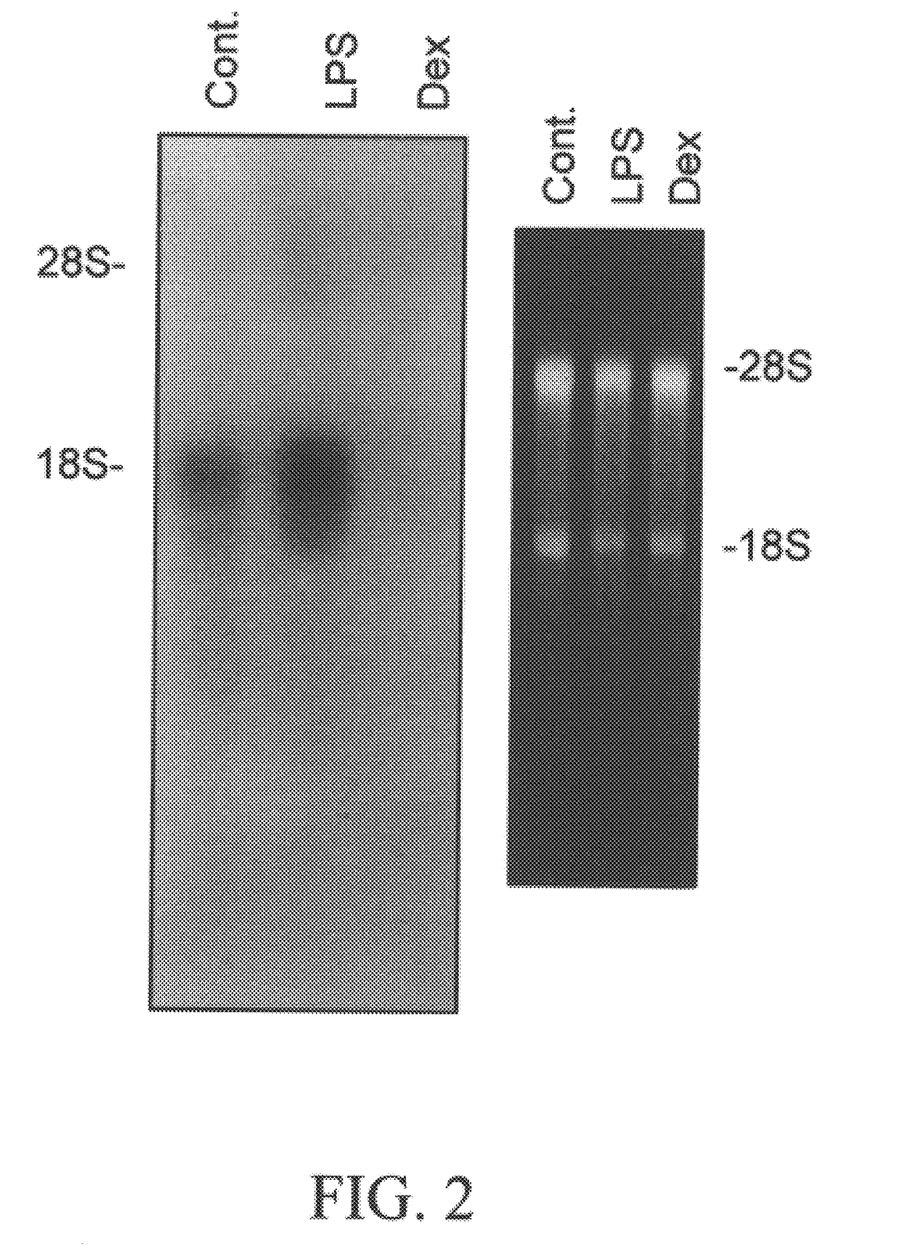
FIG. 2 shows the Northern blot analysis of mRNA derived from human alveolar macrophages.

FIG. 2. Northern blot analysis of mRNA derived from human alveolar macrophages. Human alveolar macrophages were obtained by bronchoalveolar lavage from a healthy smoker by conventional procedures as described by Shapiro et al. *J. Clin. Invest.* 86, 1204–1210 (1990). Macrophages were cultured in serum containing media for 24 hrs in the presence of no added agents (Control, Cont.), with $10^{-7}$ dexamethasone (Dex), or with 2.5 µg/ml lipopolysaccharide (LPS). Total cellular RNA was then harvested by guanidinium/acid phenol extraction, and equal amounts of RNA were subjected to Northern blot analysis with random primer labeled full-length HME cDNA as the probe. It is seen that HME cDNA hybridizes with a ~1.8 Kb mRNA, and that steady-state mRNA levels are down-regulated by dexamethasone and up-regulated by LPS. Inset: The ethidium bromide stain of the same gel demonstrates equal quality and content of the loaded RNA samples.

Figure 3A:
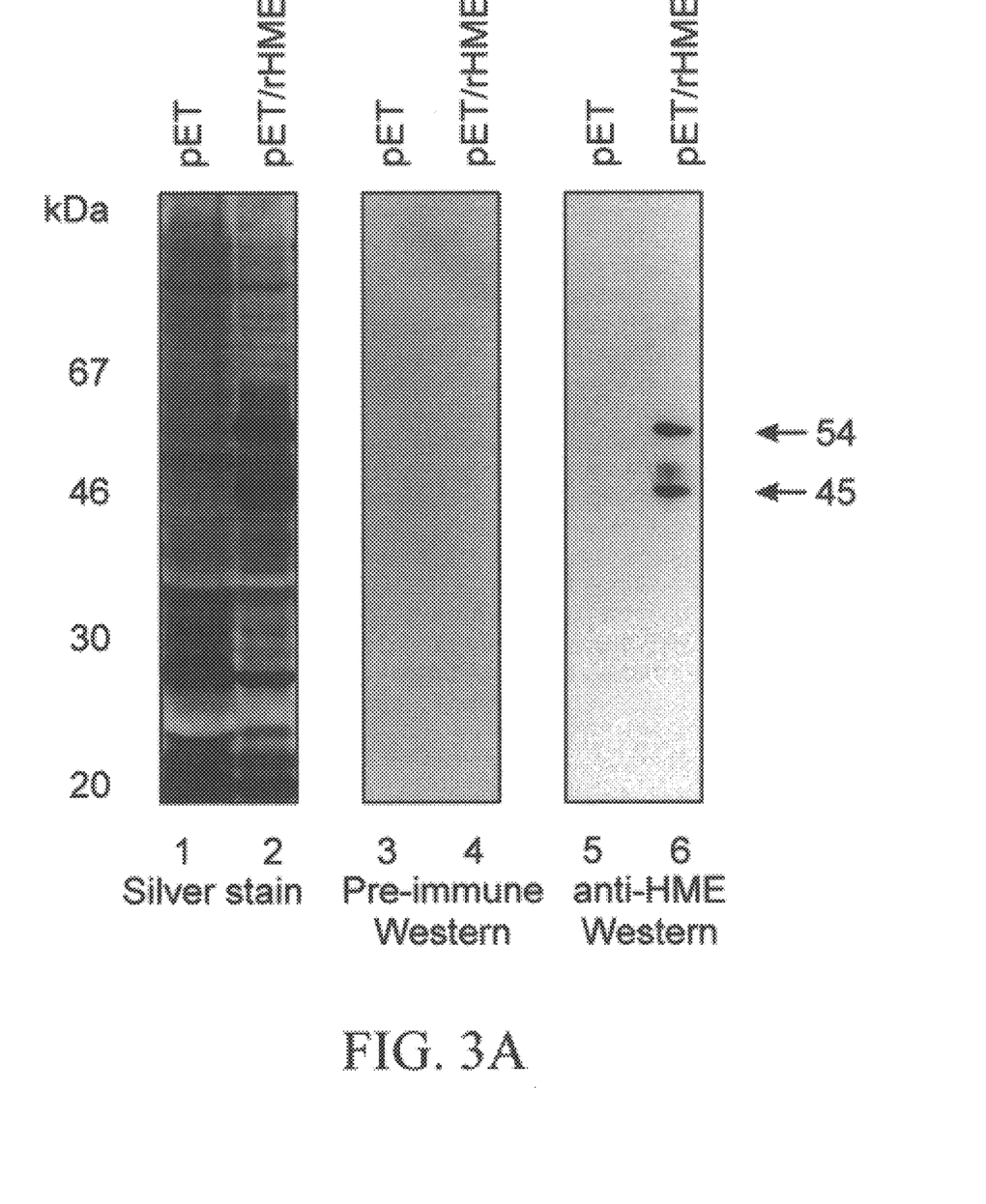
FIG. 3A shows HME cDNA ligated into the pET5B vector transformed and expressed in *E. coli*.
Figure 3B:
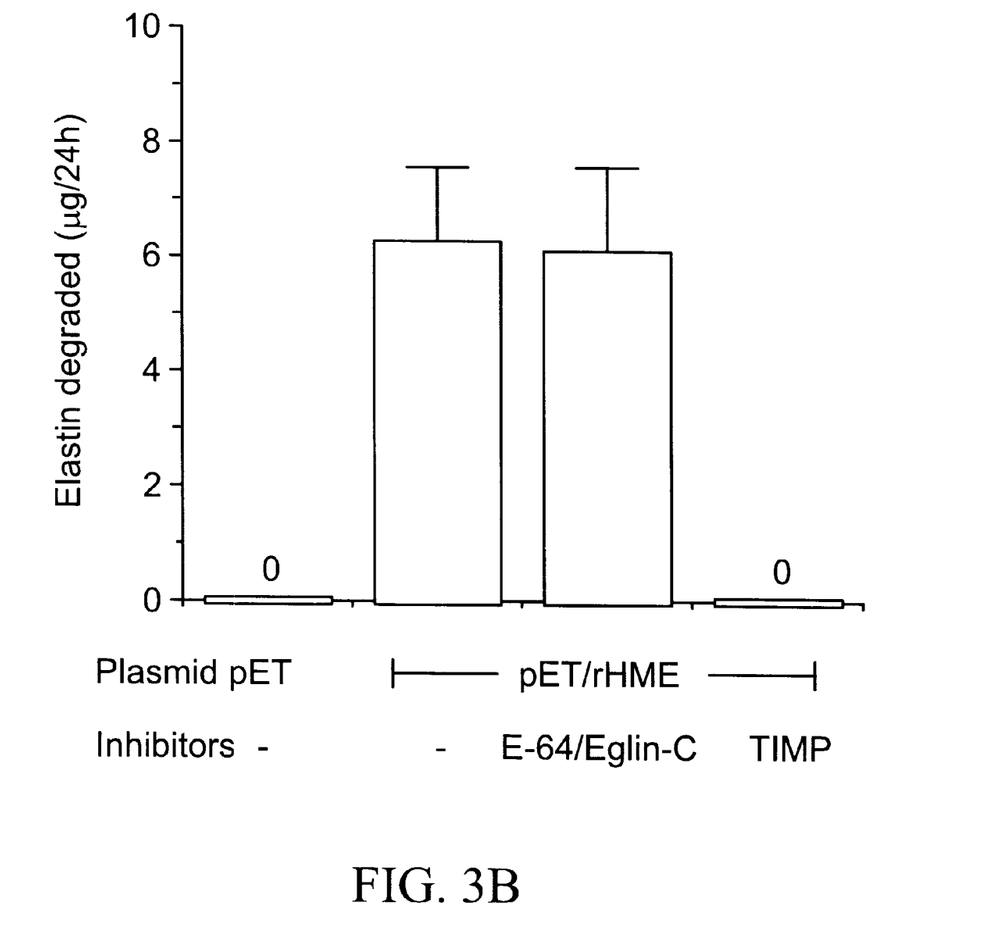
FIG. 3B is a graphical representation that shows partially purified rHME incubated on insoluble $^3$H-elastin in which elastolytic activity was quantified ($\mu$g/24 hrs) by measuring radioactivity released into the medium.

FIG. 3. Bacterial expression and elastolytic activity of recombinant HME. A. HME cDNA ligated into the pET5B vector was transformed and expressed in *E. coli* by conventional procedure as described by Shapiro et al., *J. Biol. Chem.* 267, 4664–4671 (1992). Crude lysates subjected to SDS polyacrylamide gel electrophoresis and silver staining demonstrate the appearance of additional bands at 54 and 45 kDa with expression of rHME (lane 1, pET vs lane 2, pET/rHME). Western hybridizations were performed on denatured cell extracts in the absence (pET alone) or presence of recombinant HME (pET/rHME). Preimmune serum failed to react with *E. coli* proteins or rHME (lanes 3 and 4). An HME-specific antibody did not detect control *E. coli* proteins (pET, lane 5), but identified the rHME proenzyme (54 kDa, top arrow lane 6) and N-terminal active form (45 kDa bottom arrow lane 6), as well as probable intermediate cleavage products. B. Partially purified rHME was incubated on insoluble $^3$H-elastin and elastolytic activity was quantified by measuring radioactivity released into the medium by conventional procedures as previously described by Shapiro et al., *Ibid.* and Senior et al., *Am. Rev. Respir. Dis.* 139, 251–1256 (1989). Control extract (pET) had no elastolytic activity, rHME-containing extract degraded significant amounts of insoluble elastin (pET/rHME). Serine and cysteine proteinase inhibitors (Eglin C and E-64) failed to alter elastolysis but molar excess TIMP-1 entirely inhibited pET/rHME-mediated elastin degradation. Data are expressed as micrograms of elastin degraded +/−S.D. based on cpm of triplicate samples (1 µg of elastin is represented by 1100 cpm). Similar results were obtained in 10 separate tests. Methods: Crude *E. coli* lysates were used for Western blots (panel A). rHME was solubilized, refolded, and partially purified over a heparin-agarose column as described for MME, Shapiro et al., *Ibid.*, for activity (panel B). Western hybridization was performed with the ECL detection kit (Amersham, Buckinghamshire, England) using an antibody raised in rabbits by injection of a peptide derived from the first 12 amino acids of the active N-terminal form of HME (antibodies used at a 1/10,000 dilution). The peptide antibody (1:500 dilution) specifically reacted with the rHME but did not react with 2 µg of other metalloproteinases (interstitial collagenase, stromelysin-1, matrilysin, and 92 kDa gelatinase) as determined by Western blotting.

FIG. 4. HME secretion, processin, and elastolytic activity from human alveolar macrophages. A. Human alveolar macrophages were obtained by bronchoalveolar lavage from a healthy cigarette smoker as in FIG. 2, above. Macrophages were cultured in serum-containing media for 48 hrs. HME was partially purified from conditioned media as described below, and Western hybridizations were performed (as in FIG. 3). Lane 1 and 2: Preimmune serum (1:2000 dilution) blotted against proteins obtained from conditioned media in the presence of EDTA (Lane 1) or trypsin activated (Lane 2). Lane 3: Proteins from conditioned media in the presence of 10 MM EDTA (to prevent spontaneous activation) were blotted with the peptide antibody directed against HME (1:8,000 dilution). Lane 4: Trypsin activated HME in conditioned media blotted with the peptide antibody to HME (1:8,000 dilution). It is seen that EDTA prevents activation resulting in detection of the proenzyme migrating at a molecular mass ~54 kDa (top arrow) and small amounts of N-terminal activated ~45 kDa protein (middle arrow). Trypsin activation (10 µg at 25° C., 5 min., in the absence of EDTA) converts HME to the truncated mature 22 kDa protein (lower arrow). B. Aliquots of HME-containing conditioned media following removal of gelatinase and inhibitors were incubated with insoluble $^3$H-elastin for 48 hrs at 37° C. Solubilized products were counted in a liquid scintillation counter to estimate degradation of elastin (see FIG. 3). It is seen that purification and incubation with $^3$H-elastin in the presence of EDTA maintains the proenzyme form and prevents elastolysis. Purification in the absence of EDTA causes spontaneous processing of HME associated with significant elastin degradation. Activity is inhibited by TIMP-1 but not serine (EglinC) or cysteine proteinase inhibitors (E-64). This activity is believed to be due to HME, although one cannot exclude the possible presence of yet another unrecognized metalloelastase with similar purification and activation properties. Data are expressed as µg of elastin degraded +/−S.D. of triplicate samples. Methods. Macrophage conditioned media was subjected to gelatin-agarose affinity chromatography to remove all 92 kDa and trade 72 kDa gelatinase (no gelatinase activity was detected in gelatin-agarose flow-through by gelatin zymography, <ng sensitivity). Heparin-agarose chromatography was performed on the flow-through fractions; HME eluted with 0.9 to 1.0 M NaCl (similar to NME). This fraction contained the predominant immunoreactive HME and elastolytic activity present in heparin-agarose fractions eluted with a linear salt gradient. Preparation of macrophages from five different volunteers who smoke cigarettes yielded identical results.

The invention described herein thus comprises a unique human metalloelastase expressed by human alveolar macrophages. Metalloproteinases (MMPs) comprise a family of structurally related matrix degrading enzymes that play a major role in tissue remodeling and repair associated with development and inflammation [Matresian, *Trends Genet*. 6, 121–125 (1990); and Woessner, *FASEB J*. 5, 2145–2154 (1991)]. Abnormal expression of MMPs can contribute to destructive processes including tumor invasiveness [Mignatti and Rifkin, *Cell*. 47, 487–498 (1986) and Khokha et al., *Science* 243, 947–950 (1989)], arthritis [Dean et al., *J. Clin. Invest*. 84, 678–685 (1989) and McCachren, *Arthritis Rheum*. 34, 1085–1093 (1991)], and atherosclerosis [Henney et al., *Proc. Natl. Acad. Sci. USA*, 88, 8154–8158 (1991)]. It is believed that this newly described metalloelastase—HME—is a candidate gene contributing to the pathogenesis of emphysema and other inflammatory destructive diseases.

Alveolar macrophages used for the foregoing examples were derived from healthy cigarette smokers in order to maximize the yield. Non-smokers may also express this enzyme, albeit from a much smaller and potentially less activated macrophage pool.

Various other examples will be apparent to the person skilled in the art after reading the present disclosure without departing from the spirit and scope of the invention. It is intended that all such other examples be included within the scope of the appended claims.

What is claimed is:

1. An isolated cDNA that encodes for the 470 amino acid human macrophage metalloelastase (HME) shown in FIG. 1A SEQ ID NO:2.

2. Isolated cDNA having the nucleotide sequence of basepairs 1–1410 shown in FIGS. 5A to 5D SEQ ID NO:1.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1410 base pairs
      (B) TYPE: nucleic acid
      (C) STRANDEDNESS: double
      (D) TOPOLOGY: linear    (ii) MOLECULE TYPE: cDNA    (ix) FEATURE:
      (A) NAME/KEY: CDS
      (B) LOCATION: 1..1410

(xi) SEQUENCE DESCRIPTION: SEQ ID NO:1:

```
ATG AAG TTT CTT CTA ATA CTG CTC CTG CAG GCC ACT GCT TCT GGA GCT        48
Met Lys Phe Leu Leu Ile Leu Leu Leu Gln Ala Thr Ala Ser Gly Ala
  1               5                  10                  15

CTT CCC CTG AAC AGC TCT ACA AGC CTG GAA AAA AAT AAT GTG CTA TTT        96
Leu Pro Leu Asn Ser Ser Thr Ser Leu Glu Lys Asn Asn Val Leu Phe
             20                  25                  30

GGT GAG AGA TAC TTA GAA AAA TTT TAT GGC CTT GAG ATA AAC AAA CTT       144
Gly Glu Arg Tyr Leu Glu Lys Phe Tyr Gly Leu Glu Ile Asn Lys Leu
         35                  40                  45

CCA GTG ACA AAA ATG AAA TAT AGT GGA AAC TTA ATG AAG GAA AAA ATC       192
Pro Val Thr Lys Met Lys Tyr Ser Gly Asn Leu Met Lys Glu Lys Ile
 50                  55                  60

CAA GAA ATG CAG CAC TTC TTG GGT CTG AAA GTG ACC GGG CAA CTG GAC       240
Gln Glu Met Gln His Phe Leu Gly Leu Lys Val Thr Gly Gln Leu Asp
 65                  70                  75                  80

ACA TCT ACC CTG GAG ATG ATG CAC GCA CCT CGA TGT GGA GTC CCC GAT       288
Thr Ser Thr Leu Glu Met Met His Ala Pro Arg Cys Gly Val Pro Asp
                 85                  90                  95

GTC CAT CAT TTC AGG GAA ATG CCA GGG GGG CCC GTA TGG AGG AAA CAT       336
Val His His Phe Arg Glu Met Pro Gly Gly Pro Val Trp Arg Lys His
            100                 105                 110

TAT ATC ACC TAC AGA ATC AAT AAT TAC ACA CCT GAC ATG AAC CGT GAG       384
Tyr Ile Thr Tyr Arg Ile Asn Asn Tyr Thr Pro Asp Met Asn Arg Glu
        115                 120                 125
```

```
                                                                -continued

GAT GTT GAC TAC GCA ATC CGG AAA GCT TTC CAA GTA TGG AGT AAT GTT        432
Asp Val Asp Tyr Ala Ile Arg Lys Ala Phe Gln Val Trp Ser Asn Val
    130                 135                 140

ACC CCC TTG AAA TTC AGC AAG ATT AAC ACA GGC ATG GCT GAC ATT TTG        480
Thr Pro Leu Lys Phe Ser Lys Ile Asn Thr Gly Met Ala Asp Ile Leu
145                 150                 155                 160

GTG GTT TTT GCC CGT GGA GCT CAT GGA GAC TTC CAT GCT TTT GAT GGC        528
Val Val Phe Ala Arg Gly Ala His Gly Asp Phe His Ala Phe Asp Gly
                165                 170                 175

AAA GGT GGA ATC CTA GCC CAT GCT TTT GGA CCT GGA TCT GGC ATT GGA        576
Lys Gly Gly Ile Leu Ala His Ala Phe Gly Pro Gly Ser Gly Ile Gly
            180                 185                 190

GGG GAT GCA CAT TTC GAT GAG GAC GAA TTC TGG ACT ACA CAT TCA GGA        624
Gly Asp Ala His Phe Asp Glu Asp Glu Phe Trp Thr Thr His Ser Gly
        195                 200                 205

GGC ACA AAC TTG TTC CTC ACT GCT GTT CAC GAG ATT GGC CAT TCC TTA        672
Gly Thr Asn Leu Phe Leu Thr Ala Val His Glu Ile Gly His Ser Leu
    210                 215                 220

GGT CTT GGC CAT TCT AGT GAT CCA AAG GCT GTA ATG TTC CCC ACC TAC        720
Gly Leu Gly His Ser Ser Asp Pro Lys Ala Val Met Phe Pro Thr Tyr
225                 230                 235                 240

AAA TAT GTC GAC ATC AAC ACA TTT CGC CTC TCT GCT GAT GAC ATA CGT        768
Lys Tyr Val Asp Ile Asn Thr Phe Arg Leu Ser Ala Asp Asp Ile Arg
                245                 250                 255

GGC ATT CAG TCC CTG TAT GGA GAC CCA AAA GAG AAC CAA CGC TTG CCA        816
Gly Ile Gln Ser Leu Tyr Gly Asp Pro Lys Glu Asn Gln Arg Leu Pro
            260                 265                 270

AAT CCT GAC AAT TCA GAA CCA GCT CTC TGT GAC CCC AAT TTG AGT TTT        864
Asn Pro Asp Asn Ser Glu Pro Ala Leu Cys Asp Pro Asn Leu Ser Phe
        275                 280                 285

GAT GCT GTC ACT ACC GTG GGA AAT AAG ATC TTT TTC TTC AAA GAC AGG        912
Asp Ala Val Thr Thr Val Gly Asn Lys Ile Phe Phe Phe Lys Asp Arg
    290                 295                 300

TTC TTC TGG CTG AAG GTT TCT GAG AGA CCA AAG ACC AGT GTT AAT TTA        960
Phe Phe Trp Leu Lys Val Ser Glu Arg Pro Lys Thr Ser Val Asn Leu
305                 310                 315                 320

ATT TCT TCC TTA TGG CCA ACC TTG CCA TCT GGC ATT GAA GCT GCT TAT       1008
Ile Ser Ser Leu Trp Pro Thr Leu Pro Ser Gly Ile Glu Ala Ala Tyr
                325                 330                 335

GAA ATT GAA GCC AGA AAT CAA GTT TTT CTT TTT AAA GAT GAC AAA TAC       1056
Glu Ile Glu Ala Arg Asn Gln Val Phe Leu Phe Lys Asp Asp Lys Tyr
            340                 345                 350

TGG TTA ATT AGC AAT TTA AGA CCA GAG CCA AAT TAT CCC AAG AGC ATA       1104
Trp Leu Ile Ser Asn Leu Arg Pro Glu Pro Asn Tyr Pro Lys Ser Ile
        355                 360                 365

CAT TCT TTT GGT TTT CCT AAC TTT GTG AAA AAA ATT GAT GCA GCT GTT       1152
His Ser Phe Gly Phe Pro Asn Phe Val Lys Lys Ile Asp Ala Ala Val
    370                 375                 380

TTT AAC CCA CGT TTT TAT AGG ACC TAC TTC TTT GTA GAT AAC CAG TAT       1200
Phe Asn Pro Arg Phe Tyr Arg Thr Tyr Phe Phe Val Asp Asn Gln Tyr
385                 390                 395                 400

TGG AGG TAT GAT GAA AGG AGA CAG ATG ATG GAC CCT GGT TAT CCC AAA       1248
Trp Arg Tyr Asp Glu Arg Arg Gln Met Met Asp Pro Gly Tyr Pro Lys
                405                 410                 415

CTG ATT ACC AAG AAC TTC CAA GGA ATC GGG CCT AAA ATT GAT GCA GTC       1296
Leu Ile Thr Lys Asn Phe Gln Gly Ile Gly Pro Lys Ile Asp Ala Val
            420                 425                 430

TTC TAT TCT AAA AAC AAA TAC TAC TAT TTC TTC CAA GGA TCT AAC CAA       1344
Phe Tyr Ser Lys Asn Lys Tyr Tyr Tyr Phe Phe Gln Gly Ser Asn Gln
```

-continued

```
              435                 440                 445
TTT GAA TAT GAC TTC CTA CTC CAA CGT ATC ACC AAA ACA CTG AAA AGC         1392
Phe Glu Tyr Asp Phe Leu Leu Gln Arg Ile Thr Lys Thr Leu Lys Ser
              450                 455                 460

AAT AGC TGG TTT GGT TGT                                                 1410
Asn Ser Trp Phe Gly Cys
465                 470
```

(2) INFORMATION FOR SEQ ID NO:2:

(i) SEQUENCE CHARACTERISTICS:
        (A) LENGTH: 470 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Lys Phe Leu Leu Ile Leu Leu Leu Gln Ala Thr Ala Ser Gly Ala
 1               5                  10                  15

Leu Pro Leu Asn Ser Ser Thr Ser Leu Glu Lys Asn Asn Val Leu Phe
                20                  25                  30

Gly Glu Arg Tyr Leu Glu Lys Phe Tyr Gly Leu Glu Ile Asn Lys Leu
            35                  40                  45

Pro Val Thr Lys Met Lys Tyr Ser Gly Asn Leu Met Lys Glu Lys Ile
        50                  55                  60

Gln Glu Met Gln His Phe Leu Gly Leu Lys Val Thr Gly Gln Leu Asp
65                  70                  75                  80

Thr Ser Thr Leu Glu Met Met His Ala Pro Arg Cys Gly Val Pro Asp
                85                  90                  95

Val His His Phe Arg Glu Met Pro Gly Gly Pro Val Trp Arg Lys His
            100                 105                 110

Tyr Ile Thr Tyr Arg Ile Asn Asn Tyr Thr Pro Asp Met Asn Arg Glu
        115                 120                 125

Asp Val Asp Tyr Ala Ile Arg Lys Ala Phe Gln Val Trp Ser Asn Val
    130                 135                 140

Thr Pro Leu Lys Phe Ser Lys Ile Asn Thr Gly Met Ala Asp Ile Leu
145                 150                 155                 160

Val Val Phe Ala Arg Gly Ala His Gly Asp Phe His Ala Phe Asp Gly
                165                 170                 175

Lys Gly Gly Ile Leu Ala His Ala Phe Gly Pro Gly Ser Gly Ile Gly
            180                 185                 190

Gly Asp Ala His Phe Asp Glu Asp Glu Phe Trp Thr Thr His Ser Gly
        195                 200                 205

Gly Thr Asn Leu Phe Leu Thr Ala Val His Glu Ile Gly His Ser Leu
    210                 215                 220

Gly Leu Gly His Ser Ser Asp Pro Lys Ala Val Met Phe Pro Thr Tyr
225                 230                 235                 240

Lys Tyr Val Asp Ile Asn Thr Phe Arg Leu Ser Ala Asp Asp Ile Arg
                245                 250                 255

Gly Ile Gln Ser Leu Tyr Gly Asp Pro Lys Glu Asn Gln Arg Leu Pro
            260                 265                 270

Asn Pro Asp Asn Ser Glu Pro Ala Leu Cys Asp Pro Asn Leu Ser Phe
        275                 280                 285

Asp Ala Val Thr Thr Val Gly Asn Lys Ile Phe Phe Phe Lys Asp Arg
    290                 295                 300
```

```
Phe Phe Trp Leu Lys Val Ser Glu Arg Pro Lys Thr Ser Val Asn Leu
305                 310                 315                 320

Ile Ser Ser Leu Trp Pro Thr Leu Pro Ser Gly Ile Glu Ala Ala Tyr
            325                 330                 335

Glu Ile Glu Ala Arg Asn Gln Val Phe Leu Phe Lys Asp Asp Lys Tyr
                340                 345                 350

Trp Leu Ile Ser Asn Leu Arg Pro Glu Pro Asn Tyr Pro Lys Ser Ile
            355                 360                 365

His Ser Phe Gly Phe Pro Asn Phe Val Lys Lys Ile Asp Ala Ala Val
    370                 375                 380

Phe Asn Pro Arg Phe Tyr Arg Thr Tyr Phe Val Asp Asn Gln Tyr
385                 390                 395                 400

Trp Arg Tyr Asp Glu Arg Arg Gln Met Met Asp Pro Gly Tyr Pro Lys
                405                 410                 415

Leu Ile Thr Lys Asn Phe Gln Gly Ile Gly Pro Lys Ile Asp Ala Val
            420                 425                 430

Phe Tyr Ser Lys Asn Lys Tyr Tyr Tyr Phe Gln Gly Ser Asn Gln
                435                 440                 445

Phe Glu Tyr Asp Phe Leu Leu Gln Arg Ile Thr Lys Thr Leu Lys Ser
450                 455                 460

Asn Ser Trp Phe Gly Cys
465                 470

(2) INFORMATION FOR SEQ ID NO:3:

(i) SEQUENCE CHARACTERISTICS:
        (A) LENGTH: 462 amino acids
        (B) TYPE: amino acid
        (D) TOPOLOGY: linear (ii) MOLECULE TYPE: peptide (xi) SEQUENCE DESCRIPTION: SEQ ID NO:3:

Met Lys Phe Leu Met Met Ile Val Phe Leu Gln Val Ser Ala Cys Gly
1               5                   10                  15

Ala Ala Pro Met Asn Asp Ser Glu Phe Ala Glu Trp Tyr Leu Ser Arg
                20                  25                  30

Phe Tyr Asp Tyr Gly Lys Asp Arg Ile Pro Met Thr Lys Thr Lys Thr
            35                  40                  45

Asn Arg Asn Phe Leu Lys Glu Lys Leu Gln Glu Met Gln Gln Phe Phe
        50                  55                  60

Gly Leu Glu Ala Thr Gly Gln Leu Asp Asn Ser Thr Leu Ala Ile Met
65                  70                  75                  80

His Ile Pro Arg Cys Gly Val Pro Asp Val Gln His Leu Arg Ala Val
                85                  90                  95

Pro Gln Arg Ser Arg Trp Met Lys Arg Tyr Leu Thr Tyr Arg Ile Tyr
                100                 105                 110

Asn Tyr Thr Pro Asp Met Lys Arg Glu Asp Val Asp Tyr Ile Phe Gln
            115                 120                 125

Lys Ala Phe Gln Val Trp Ser Asp Val Thr Pro Leu Arg Phe Arg Lys
130                 135                 140

Leu His Lys Asp Glu Ala Asp Ile Met Ile Leu Phe Ala Phe Gly Ala
145                 150                 155                 160

His Gly Asp Phe Asn Tyr Phe Asp Gly Lys Gly Gly Thr Leu Ala His
                165                 170                 175

Val Phe Tyr Pro Gly Pro Gly Ile Gln Gly Asp Ala His Phe Asp Glu
```

-continued

```
                  180                 185                 190
Ala Glu Thr Trp Thr Lys Ser Phe Gln Gly Thr Asn Leu Phe Leu Val
            195                 200                 205
Ala Val His Glu Leu Gly His Ser Leu Gly Leu Gln His Ser Asn Asn
        210                 215                 220
Pro Lys Ser Ile Met Tyr Pro Thr Tyr Arg Tyr Leu Asn Pro Ser Thr
225                 230                 235                 240
Phe Arg Leu Ser Ala Asp Asp Ile Arg Asn Ile Gln Ser Leu Tyr Gly
                245                 250                 255
Ala Pro Val Lys Pro Pro Ser Leu Thr Lys Pro Ser Ser Pro Pro Ser
                260                 265                 270
Thr Phe Cys His Gln Ser Leu Ser Phe Asp Ala Val Thr Thr Val Gly
                275                 280                 285
Glu Lys Ile Leu Phe Phe Lys Asp Trp Phe Phe Trp Trp Lys Leu Pro
        290                 295                 300
Gly Ser Pro Ala Thr Asn Ile Thr Ser Ile Ser Ser Ile Trp Pro Ser
305                 310                 315                 320
Ile Pro Ser Ala Ile Gln Ala Ala Tyr Glu Ile Glu Ser Arg Asn Gln
                325                 330                 335
Leu Phe Leu Phe Lys Asp Glu Lys Tyr Trp Leu Ile Asn Asn Leu Val
                340                 345                 350
Pro Glu Pro His Tyr Pro Arg Ser Ile Tyr Ser Leu Gly Phe Ser Ala
                355                 360                 365
Ser Val Lys Lys Val Asp Ala Ala Val Phe Asp Pro Leu Arg Gln Lys
            370                 375                 380
Val Tyr Phe Phe Val Asp Lys His Tyr Trp Arg Tyr Asp Val Arg Gln
385                 390                 395                 400
Glu Leu Met Asp Pro Ala Tyr Pro Lys Leu Phe Ser Thr His Phe Pro
                405                 410                 415
Gly Ile Lys Pro Lys Ile Asp Ala Val Leu Tyr Phe Lys Arg His Tyr
                420                 425                 430
Tyr Ile Phe Gln Gly Ala Tyr Gln Leu Glu Tyr Asp Pro Leu Phe Arg
            435                 440                 445
Arg Val Thr Lys Thr Leu Lys Ser Thr Ser Trp Phe Gly Cys
    450                 455                 460
```